US006258039B1

(12) United States Patent
Okamoto et al.

(10) Patent No.: US 6,258,039 B1
(45) Date of Patent: Jul. 10, 2001

(54) RESPIRATORY GAS CONSUMPTION MONITORING DEVICE AND MONITORING METHOD

(75) Inventors: Mineo Okamoto; Hitoshi Yamaguchi, both of Yokosuka; Yoshikazu Shirane; Kenji Demura, both of Tokyo, all of (JP)

(73) Assignees: Nippon Sanso Corporation, Tokyo; Japan Marine Science and Technology Center, Kanagawa, both of (JP)

( * ) Notice: Subject to any disclaimer, the term of this patent is extended or adjusted under 35 U.S.C. 154(b) by 0 days.

(21) Appl. No.: 09/381,653

(22) PCT Filed: Jan. 14, 1999

(86) PCT No.: PCT/JP99/00093

§ 371 Date: Sep. 20, 1999

§ 102(e) Date: Sep. 20, 1999

(87) PCT Pub. No.: WO99/36128

PCT Pub. Date: Jul. 22, 1999

(30) Foreign Application Priority Data

Jan. 19, 1998 (JP) ................................................ 10-008093

(51) Int. Cl.[7] ........................................................ A61B 5/08

(52) U.S. Cl. ............................................................ 600/529

(58) Field of Search .................................... 600/529, 532, 600/531, 538; 128/204.21, 204.23

(56) References Cited

U.S. PATENT DOCUMENTS 4,619,269 * 10/1986 Cutler et al. ......................... 600/532
4,686,974 * 8/1987 Sato et al. ....................... 128/204.23
5,540,220 * 7/1996 Gropper et al. ................ 128/204.23
5,694,924 * 12/1997 Cewers ........................... 128/204.21

* cited by examiner

*Primary Examiner*—Robert L. Nasser
*Assistant Examiner*—Brian Szmal
(74) *Attorney, Agent, or Firm*—Darby & Darby

(57) ABSTRACT

The present invention relates to a respiratory gas consumption monitoring method and monitoring device that is portable and has high measurement accuracy, for enabling the analysis and prediction of the respiratory behavior of subjects employing a variety of different types of breathing apparatuses in water, etc. Respiratory gas consumption monitoring device (20), for monitoring the respiratory gas consumption of the user of a breathing apparatus (1) in which a respiratory gas (G) inside a high pressure gas container (2) is reduced in pressure at pressure regulator (4) and supplied to a breathing mask (10), is provided with:

a primary pressure sensor (21) for detecting the pressure prior to pressure reduction at pressure regulator (4);

a temperature sensor (22) for correction;

an environmental pressure sensor (23) for detecting the environmental pressure;

an amplifier (24) for amplifying the signals from the aforementioned sensors;

an A/D converter (25) for performing analog/digital conversion of the amplified signal;

a data logger (26) for recording and storing the analog/digital converted signals; and a display (27) for display.

In addition, as needed, a computer (X) for calculating, analyzing, and predicting data may be housed in housing (28), and connected to breathing apparatus (1) by connecting primary pressure sensor (21) to a high pressure opening (8) of pressure regulator (4) using a high pressure hose (29).

7 Claims, 4 Drawing Sheets

RESPIRATORY GAS CONSUMPTION MONITORING DEVICE AND MONITORING METHOD

TECHNICAL FIELD

The present invention relates to a device for measuring and monitoring consumption of the respiratory gas that is used to fill a high pressure gas container employed in such breathing apparatuses as air respirators used in land disasters, oxygen respirators used in medical treatment, or the respirators employed by scuba divers in the water. The present invention's respiratory gas consumption monitoring device may also be employed to measure and monitor changes in the user's respiratory volume, or the like. More specifically, the present invention relates to a respiratory gas consumption monitoring device and monitoring method which can be suitably employed to measure and monitor respiratory gas consumption per breath; the amount of respiratory gas used per operation of the device; and changes in respiratory volume or respiratory gas consumption which arise depending on whether or not the user is active, or on the type of activity being performed.

This specification is based on a patent application filed in Japan (Japanese Patent Application Hei 10-8093), a portion of which is incorporated herein by reference.

BACKGROUND ART

A flow meter employing a specialized sensor for capturing changes in the flow speed of a gas along a flow path, such as a hose through which the gas is flowing, is used to measure of respiratory volume, a value which is employed in the fields of medical treatment and physiological research. Respiratory flow meters such as these are (1) directly applied to the mouth of a person, (2) incorporated into the inhalation or exhalation duct system, etc., and are used for obtaining measurements in the case where the subject is a human being confined in a room where movement and activities are minimal. This type of flow meter device is not appropriate for measurements in the case where the subject is a human being who is exercising or performing activities that are accompanied by movement. In addition, in order to measure the respiratory volume of a user who is wearing the breathing apparatus, the gas circuit such as the arrangement of the piping and devices for measuring results in a large device. As a result, the device cannot be made portable for the user. Furthermore, it has been technically difficult to employ the aforementioned flow meters to measure respiratory volume in breathing apparatuses provided with a demand pressure regulator, in which respiratory gas stored at high pressure is inhaled during breathing.

A method has been attempted in which lung capacity, which is a primary factor in determining respiration in humans and animals, is estimated based on changes in form as a method for measuring respiratory volume without employing a flow meter. However, from the perspective of accuracy and practical application in the water or under other such specialized conditions, this method has not yet reached the point where it can be used in the field.

On the other hand, dive computers have been developed in recent years for scuba diving with the intention of making diving safer by preventing decompression sickness. Among these devices, there are those that measure the gas pressure (residual pressure) in the high pressure gas container. However, these devices have as their main objective the display of the gas remaining and the provision of a warning to the user, and lack the fine sensitivity or accuracy for measuring gas consumption per breath taken by the diver.

In any case, the conventional technology has not yet provided a device for directly measuring the volume of the gas itself as an indicator of the respiratory gas consumption value.

DISCLOSURE OF INVENTION

The present invention was conceived in consideration of the above-described circumstances, and has as its objective the provision of an easy-to-use respiratory gas consumption monitoring device and monitoring method that enable extremely accurate measurements, and do not require a flow meter or complicated piping, so that the device may be made small enough to enable portability by a user who is wearing it, the present invention's respiratory gas consumption monitoring device and monitoring method being intended to replace conventional methods for measuring flow speed in a piping through which gas flows, or making estimates based on changes in the human physique, which have been problematic with respect to maintaining accuracy when measuring respiratory gas consumption. As a result, the present invention aims to be used effectively as a monitoring measurement device for measuring the respiratory state of a worker performing an activity in the field, such as in the water, for grasping differences in the degree of fatigue based on the type of activity; and for investigating and clarifying the cause of the fatigue.

In order to resolve the aforementioned problems and achieve the stated objectives, the present invention's respiratory gas consumption monitoring device for a breathing apparatus reduces the pressure of respiratory gas supplied from a high pressure gas container via the use of a pressure regulator, and supplies the gas to the breathing mask worn by the user, the present invention's respiratory gas consumption monitoring device being characterized in the provision of a primary pressure sensor for detecting the primary pressure in the high pressure gas container before the pressure is reduced by the pressure regulator; an amplifier for amplifying the signal detected by the primary pressure sensor; an A/D converter for performing analog/digital conversion of the signal; a data logger for storing the analog/digital converted signals; and a display for displaying the signals or data needed for monitoring the respiratory state of the user of the breathing apparatus.

In the present invention's respiratory gas consumption monitoring device for a breathing apparatus, a primary pressure sensor may be connected to the amplifier, along with at least one of either a surrounding environmental pressure sensor and a temperature sensor for correcting the signals detected by the primary pressure sensor in accordance with the gas temperature and surrounding environmental pressure states.

In the present invention's respiratory gas consumption monitoring device for a breathing apparatus, a computer having at least one of the functions of calculating respiratory gas consumption, and the analyzing and predicting respiratory behavior may be provided connected to the data logger, which stores the analog/digitally converted signals.

The present invention's respiratory gas consumption monitoring device for a breathing apparatus may be provided with a transmitting and receiving apparatus having a function for enabling transmission and reception of data at a site which is removed from the location of the user of the breathing apparatus.

In the present invention's respiratory gas consumption monitoring device for a breathing apparatus, the signal and data displayed on the display device may be designed to display at least one signal and data for expressing the respiratory gas consumption state, respiratory behavior of the user of the breathing apparatus, or the environmental state at the location where the breathing apparatus is being used.

In the present invention's method for monitoring respiratory gas consumption using the aforementioned device, when monitoring respiratory gas consumption in a breathing apparatus in which the respiratory gas from a high pressure gas container is communicated to a breathing mask worn by the user after being reduced in pressure by a pressure regulator, the respiratory gas consumption of the user wearing the breathing apparatus is measured by detecting changes in the primary pressure of the high pressure gas container prior to reduction of the pressure by the pressure regulator.

In the present invention's method for monitoring respiratory gas consumption, the detection of changes in the primary pressure of the high pressure gas container may be measured after correcting in response to changes in the state of at least one of either the surrounding environmental pressure or the gas temperature.

The present invention's method for monitoring respiratory gas consumption is characterized in amplifying the pressure signal obtained when the primary pressure of the high pressure gas container is detected prior to pressure reduction, analog/digitally converting the signal at an A/D converter, and extracting the analog/digitally converted signal, and the signals and data needed for monitoring the respiratory and physiological state of the user wearing the breathing apparatus, or monitoring the respiratory state of the user under various environmental factors.

In addition, in the present invention's method for monitoring respiratory gas consumption, the analog/digitally converted signal, and the signals and data needed for monitoring, may be transmitted to and extracted at a monitoring base which is at a site removed from the location of the user of the breathing apparatus.

BEST MODE FOR CARRYING OUT THE INVENTION

Figure 1:
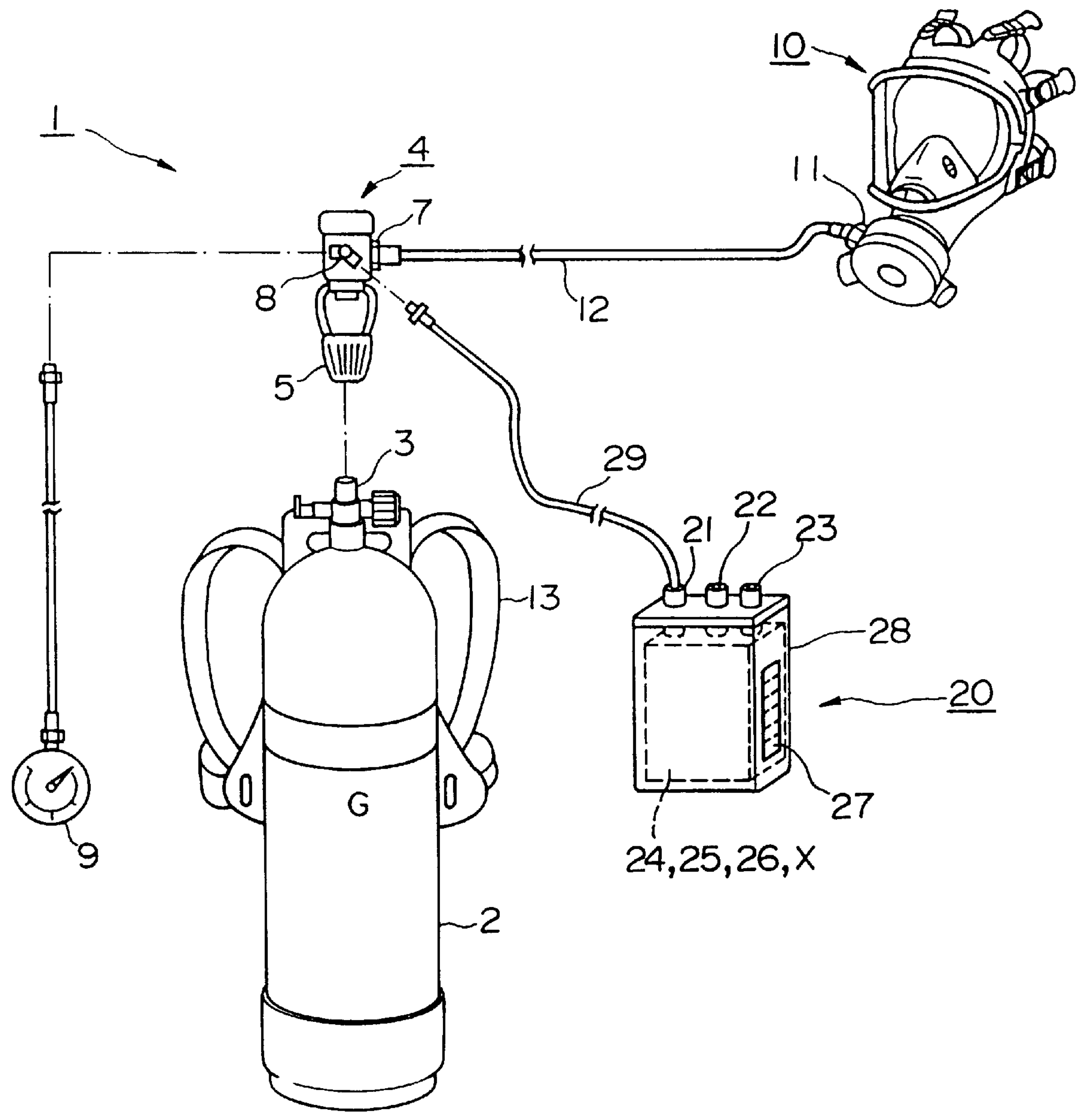
FIG. 1 is a system overview showing one example of a self-contained breathing apparatus equipped with the present invention's respiratory gas consumption monitoring device.

The meaning of "respiratory gas consumption monitoring" as used in the present invention includes both monitoring of respiratory gas consumption in the narrow sense, as well as the analysis and prediction of respiratory behavior. While it is possible to make a distinction between monitoring of respiratory gas consumption in the narrow sense of the word, and analysis and prediction of respiratory behavior, mutually overlapping technical items make discrimination impossible.

In the narrow sense of the word, monitoring comprises, first, measuring the primary pressure (charging pressure) of a high pressure gas container (gas cylinder) which is filled with the respiratory gas, or measuring the primary pressure along with the changes over time in the environmental pressure and temperature, at the site of use of the breathing apparatus, and displaying these values; and, second, calculating the respiratory gas consumption (a) from this data and from the volume of the high pressure gas container. This respiratory gas consumption can be displayed as, for example, (b) Respiratory Minute Volume (respiratory volume per minute), (c) respiratory volume per breath, (d) number of breaths per unit time, or the like. These values could also be referred to as the analysis of respiratory behavior, however. In addition, note that it is also possible to view changes in the primary pressure alone as the respiratory gas consumption. In this invention, however, both the change in the primary pressure, as well as the quantity obtained when this is converted to a gas volume, are expressed as the respiratory gas consumption (a).

Analysis and prediction of respiratory behavior can be performed after referencing the data measured at the site where the breathing apparatus is being employed, along with other data such as previous work data which has been accumulated separately for the user of the device, physiological data, and the like. The results of this analysis and prediction of respiratory behavior can be expressed as, for example, (e) an understanding of the characteristics of the breathing apparatus, (f) the relationship between activity state and the respiratory state (i.e., the respiratory state unique to diving for example), (g) the relationship between environmental factors (temperature, pressure) and the respiratory state, (h) safety management through a comparison with past data, and the like.

The measurement, analysis and prediction of respiratory behavior and respiratory gas consumption can be performed by connecting a computer to the respiratory gas consumption monitoring device. Measurement signals and data obtained at the location of use can be sent to a remote site. Calculations, analysis and predictions can be made at the remote site, with display and monitoring also carried out there. It is also possible to relay the results of calculations performed at the remote site to the respiratory gas consumption monitoring device at the location of its use, for display there.

Examples of arrangements for storing and supplying respiratory gas include a self-contained method in which the user carries a high pressure gas container, such as a small gas cylinder having a volume of 1~20 liters, that is filled with and stores the respiratory gas; and, as a concentrated method having a greater scale, a hose supplied-gas method, in which a gas storage tank is disposed at a base site as the high pressure gas container, and respiratory gas is supplied from the storage tank to a user wearing a breathing apparatus. In this latter method, the pressure (at the time of shipping) for charging the respiratory gas into the high pressure gas container is typically in the range of 150~300 $kgf/cm^2$ (gauge pressure).

The present invention's respiratory gas consumption monitoring device and monitoring method can be used for either a self-contained breathing apparatus or an outside supplied breathing apparatus.

The present invention's respiratory gas consumption monitoring device and monitoring method employ a precision pressure sensor, consisting of a semiconductor gauge for example, to measure the gas pressure ("primary pressure" hereinafter) in a high pressure gas container filled with the respiratory gas, and determine the amount of change in the primary pressure with each breath taken by the breathing apparatus's user. The present invention's respiratory gas consumption monitoring device and method are further characterized in monitoring respiratory gas consumption, and performing analysis and prediction of respiratory behavior, by simultaneously measuring the gas temperature and the surrounding environmental pressure at the location of use of the breathing apparatus, and accurately extracting the respiratory gas consumption per breath by correcting the primary pressure based on these measurements.

The present invention can determine the amount of change in the primary pressure based on a plurality of breaths or on respiration over a fixed period of time, or can determine the amount of change in the primary pressure during the interval of one operation (during one dive interval, for example). Based on these values, the present invention can monitor respiratory gas consumption, and performs analysis and prediction of respiratory behavior based on a plurality of breaths, respiration over a fixed time interval, or respiration during the interval of one operation.

Preferred embodiments of the present invention's respiratory gas consumption monitoring device will now be explained using FIG. 1, which shows a system overview of one example in which the present invention's device is provided to a self-contained breathing apparatus.

The self-contained breathing apparatus 1 shown in FIG. 1 is designed such as follows. Namely, a primary pressure regulator 4 is disposed connecting with container valve 3, which is provided to a pressure-resistant high pressure gas container 2, such as a gas cylinder, that is filled with respiratory gas G. Primary pressure regulator 4, which is for reducing the primary pressure of the high pressure gas contained in high pressure container 2, in connected to container valve 3 in an airtight manner by means of a high pressure connector 5 which is disposed to the end of primary pressure regulator 4 which is on the primary pressure side. A pressure reducing mechanism 6 (not shown in the figures) is housed inside primary pressure regulator 4 for reducing the pressure of respiratory gas G inside the high pressure gas container 2 to a specific value which is lower than the high primary pressure. Low pressure connecting hole 7 on the secondary pressure side is disposed to form a guide hole for the gas which has been reduced in pressure via the pressure reducing mechanism. Numeral 8 indicates a high pressure opening communicating with a hose on the primary pressure side. A pressure gauge 9 for measuring the pressure of the gas used to fill the high pressure gas container 2 is typically attached to high pressure opening 8.

Low pressure connecting hole 7 on the secondary pressure side of primary pressure regulator 4 is connected via pliable hose 12 to secondary pressure regulator 11, which is disposed to breathing mask 10 so as to enable the wearer of the mask to adjust the respiratory pressure during use to a suitable and comfortable level. When using a self-contained breathing apparatus 1 designed in this way, the user of the breathing apparatus transports high pressure gas container 2 by carrying it on his back or the like, puts on breathing mask 10 so that it covers his face, and adjusts the pressure using secondary pressure regulator 11 to suit his respiration.

Figure 2:
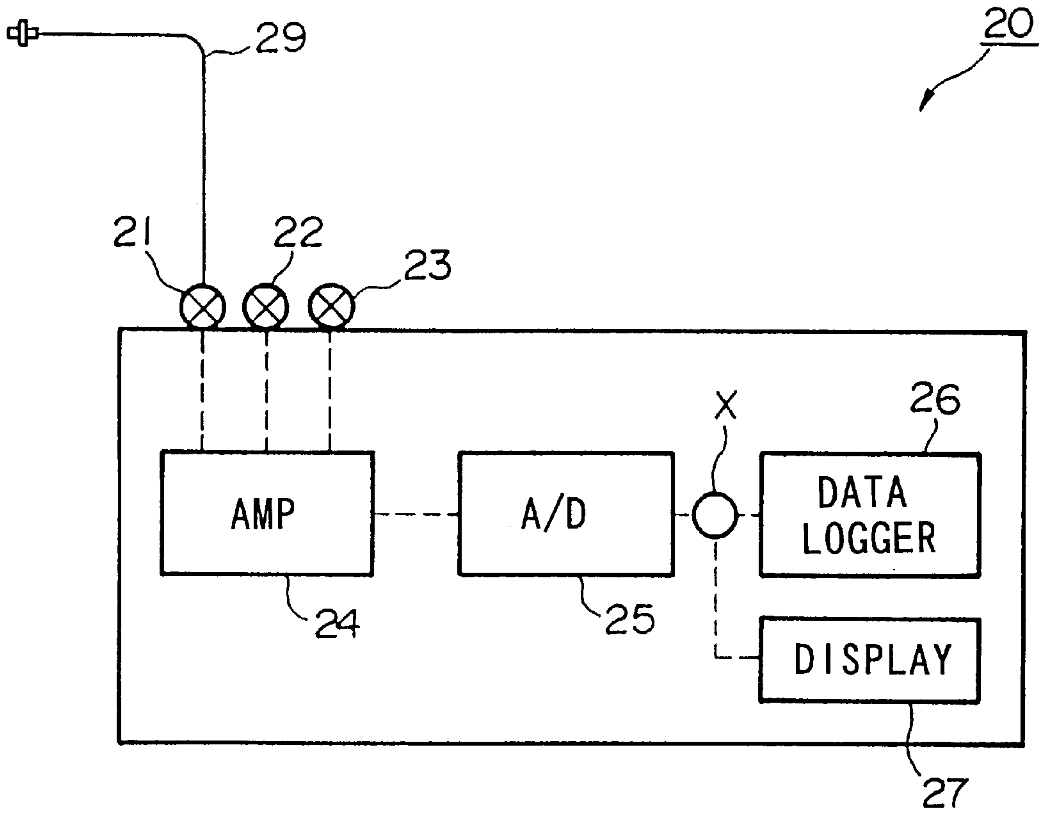
FIG. 2 is a diagram summarizing the basic configuration of the equipment circuit showing one example of the present invention's respiratory gas consumption monitoring device.

The present invention's respiratory gas consumption monitoring device 20 is provided with a primary pressure sensor 21 for measuring the primary pressure of the respiratory gas used to fill the high pressure gas container 2 of the aforementioned breathing apparatus 1; a temperature sensor 22 for measuring temperature; and an environmental pressure sensor 23 for measuring the pressure at the location of use. Monitoring of respiratory gas consumption is then performed based on the data obtained from these measurements. Further, in order to accurately extract these signals and data, the present invention's respiratory gas consumption monitoring device 20 is comprised of equipment such as shown in FIG. 2. Namely, FIG. 2 is a diagram showing an overview of the basic configuration of the equipment circuit showing one example of respiratory gas consumption monitoring device 20. The device shown in this figure comprises a primary pressure sensor 21 for measuring the primary pressure of a respiratory gas; a temperature sensor 22 for measuring the gas temperature (which essentially is the temperature of the surrounding environment in which the device is used); an environmental pressure sensor 23 for measuring the pressure of the surrounding environment in which the device is used; an amplifier 24 for amplifying the signals obtained from these sensors 21, 22, 23; an A/D converter 25 for performing analog/digital conversion of the signal amplified at device 24; data logger 26 for recording and storing the signals converted at A/D converter 25 as data; and display 27 for immediately and constantly displaying changes over time in the A/D converted signal.

A preferred arrangement of even more superior functioning may be made by incorporating a computer X in addition to the above equipment, this computer being for the purpose of calculating respiratory gas consumption, and analyzing and predicting respiratory behavior, based on data obtained from the aforementioned devices. Further, it is convenient to provide a transmitting and receiving device Y (not shown) capable of sending and receiving data and directives and replies between the user of the breathing apparatus and a remote command and monitoring base. Note that it is of course preferable that the device that is employed for display 27 be provided with a function for displaying respiratory gas consumption and the results of the analysis and prediction of respiratory behavior.

As indicated by numeral 20 in FIG. 1, in the present invention's respiratory gas consumption monitoring device consisting of the equipment circuit of the configuration shown in FIG. 2, an amplifier 24, A/D converter 25, data logger 26, display 27 and, as necessary, an optimally provided computer X, as well as other equipment, are watertightly housed in housing 28, disposed tightly together so that housing 28 can be made small and lightweight. It is necessary to design housing 28 to be resistant to the water pressure that is applied in accordance with the water depth, and so as not to leak water when employing during diving. Primary pressure sensor 21 measures the primary pressure and is disposed so as to be exposed via a high pressure hose 29 to the respiratory gas used to fill the high pressure gas container, high pressure hose 29 being connected to the high pressure opening 8 for attaching pressure gauge 9, which is for measuring the gas pressure in the high pressure gas container that is provided to primary pressure regulator 4 which is disposed to high pressure gas container 2 of breathing apparatus 1.

Note that, rather than guiding high pressure respiratory gas G via high pressure hose 29 from high pressure opening 8 of primary pressure regulator 4 as described above, it is also acceptable for primary pressure sensor 21 to attach directly to high pressure opening 8 and measure the primary pressure by being exposed to respiratory gas G, with the signal taken up inside housing 28 via a watertight cable. However, in the case of diving or the like, divers typically use a variety of respectively unique pressure regulators. While the screw sizes for high pressure opening 8 for attaching the pressure gauge are of an equivalent standard as prescribed under JIS (Japanese Industrial Standard), the pressure regulators may have a variety of shapes. When employing the present invention's respiratory gas consumption monitoring device in a variety of breathing apparatuses, in which various different types of pressure regulators may be used, it is preferable in terms of the operational efficiency to employ a method in which a high pressure hose 29 such as shown in FIG. 1 is used to guide the high pressure respiratory gas to primary pressure sensor 21, since operability of the device can be accomplished easily simply by attaching or releasing the hose. Moreover, in the case where simultaneously attaching pressure gauge 9 to high pressure opening 8, it is acceptable to provide a branch piece to the high pressure opening, as shown in the figures.

Primary pressure sensor 21 must be capable of high accuracy in the pressure range conforming to the maximum charge pressure used in high pressure gas container 2. Typically, this pressure range is preferably 0~300 kgf/cm$^2$ (gauge pressure), with an accuracy of ±0.25% {full scale (range of measured pressure)} being preferred.

Temperature sensor 22 and environmental pressure sensor 23 are disposed to the wall of housing 28 so as to be exposed to the outside air. These sensors are employed effectively during diving in particular, for measuring the water temperature and water depth. Namely, water temperature and water depth are extremely important values in the dive profile created by the diver, as well as from the perspective of the safety of that dive. Moreover, temperature sensor 22 and environmental sensor 23 are also used in the correction performed in order to obtain an accurate value for respiratory gas consumption which is determined from changes in the primary pressure.

Note that it is necessary to convert the temperature of the respiratory gas inside high pressure gas container 2 based on the temperature at the location where the breathing apparatus is being used. In the case where the device is being used in water, such as during a dive, the temperature of the respiratory gas inside high pressure gas container 2 may be considered to be approximately equal to the temperature of the water. However, for better accuracy, it is more preferable, even in water, to bring temperature sensor 22 into direct contact with the respiratory gas in order to measure the gas temperature, by using high pressure opening 8 of primary pressure regulator 4 in the same manner as employed for primary pressure sensor 21.

Each of the signals measured at primary pressure sensor 21, temperature sensor 22, and environmental pressure sensor 23 is amplified at amplifier 24, analog/digitally converted at A/D converter 25, stored in data logger 26, and then displayed in detail on display 27. As a result, the user is able to understand and confirm his current state. Note that the measured values obtained from the aforementioned sensors may be stored and displayed as data without modification. However, a preferred arrangement of even superior functionality may be made by incorporating a computer X for calculating the specific respiratory gas consumption, or analyzing and predicting respiratory behavior. Further, it is convenient to provide a transmitting and receiving device Y (not shown) capable of sending and receiving data and directives and replies between the user of the breathing apparatus and a remote command and inspection base. Note that it is of course preferable that a device is employed for display 27 which is provided with a function for displaying respiratory gas consumption and the results of the analysis and prediction of respiratory behavior.

As discussed above, the present invention's respiratory gas monitoring device 20 is organically connected to a breathing apparatus 1, and is made small and lightweight enough so that the user can engage is sufficiently active operations at a site. This respiratory gas consumption monitoring device 20 renders possible such functions as accurately measuring and storing the minimum required state quantities, such as primary pressure, gas temperature, and environmental pressure, for monitoring respiratory gas consumption when the user is in a state of activity. The measured and stored data can be immediately analyzed, or analyzed following recovery and then applied in safety management. The measured and stored data may also be used effectively to obtain a technical evaluation of the breathing apparatus, to grasp the supply state of the respiratory gas depending on different work activities performed by the user, or to educate and train workers.

Note that the present invention's respiratory gas consumption monitoring device and w monitoring method were explained using an example in which a self-contained breathing apparatus was employed. However, the present invention is not limited thereto, but may also be employed in an outside supplied breathing apparatus. Moreover, the present invention's respiratory gas consumption monitoring device and monitoring method may be suitably employed at any type of sites where a breathing apparatus is employed, such as, for example, during diving, in land disasters, in medical treatment (i.e., extraction of a life vitality signal using respiratory monitoring of a patient inhaling oxygen), in training to acclimate to low oxygen environments, or in monitoring in sports medicine.

In addition, by determining respiratory volume through the addition of this function to the dive computers which have spread in use in recent years, it is possible to more accurately manage decompression, so that the diver's safety is improved.

EXAMPLES

Next, examples of the present invention's respiratory gas consumption monitoring device will be explained.

An experimental device having the specifications as follows was used as a respiratory gas consumption monitoring device during diving. The device was connected to a self-contained breathing apparatus consisting of a 10 liter high pressure gas container (gas cylinder) such as shown in FIG. 1, and diving was performed.

<Specifications for housing 28>

- width: 150 mm
- height: 250 mm square
- material: synthetic resin (5 mm thick acrylic resin)
- thickness: 80 mm <Installed equipment>

- Primary pressure sensor (semiconductor strain gauge)
- Temperature sensor (semiconductor temperature sensor)
- Environmental pressure sensor (semiconductor strain gauge)
- Amplifier
- A/D converter
- Data logger
- Display <Weight (configuration loaded with equipment)>

Figure 3:
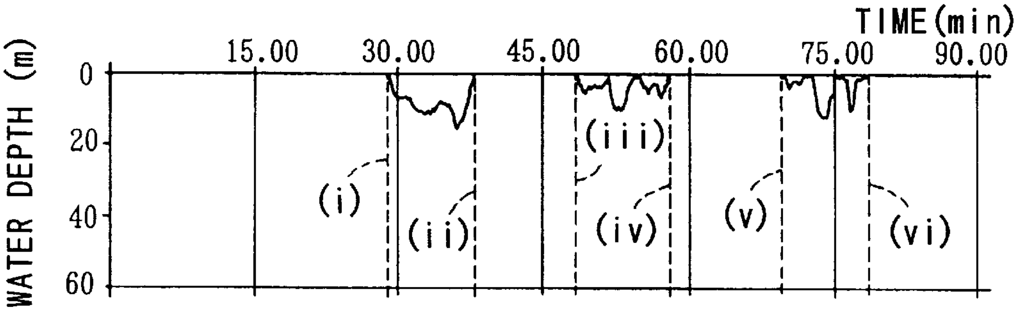
FIG. 3 is a graph of water depth measurements when diving which were obtained in the examples employing the present invention's respiratory gas consumption monitoring device underwater.
Figure 4:
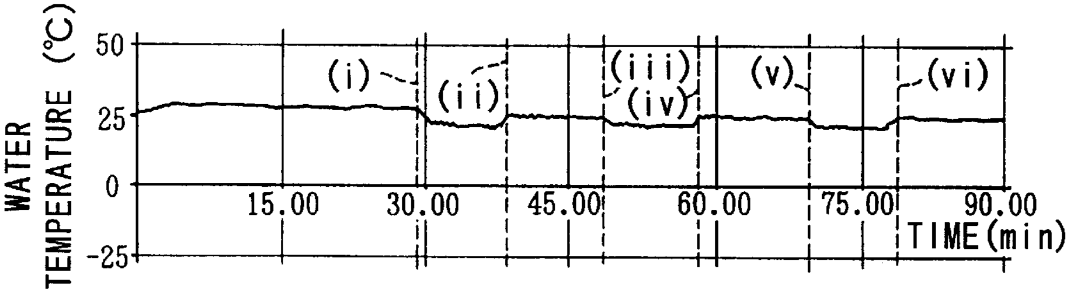
FIG. 4 is a graph of water temperature measurements when diving which were obtained in the examples employing the present invention's respiratory gas consumption monitoring device underwater.
Figure 5:
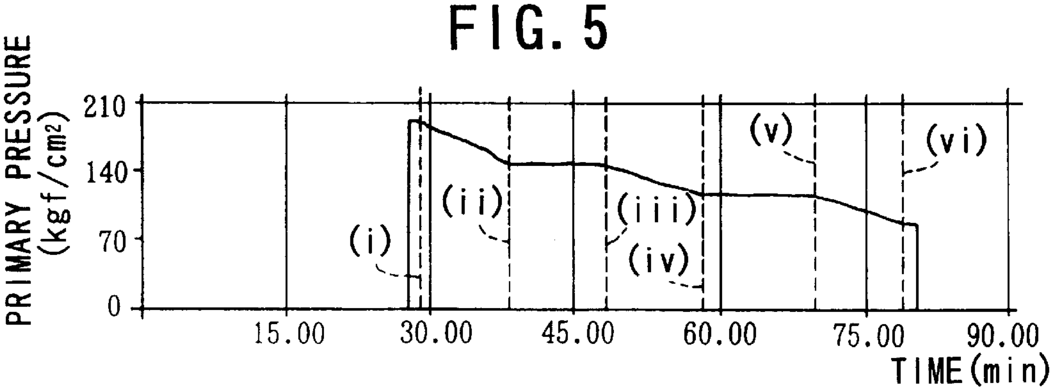
FIG. 5 is a graph of measurements of the primary pressure in a high pressure gas container when diving which were obtained in the examples employing the present invention's respiratory gas consumption monitoring device underwater.

- weight at atmospheric pressure: 3.5 kg
- weight in water: approximately neutral buoyancy, did not constitute added load to
- buoyancy adjustments typically made by diver Three intermittent dives were carried out using the above-described experimental device. The data which was detected by primary pressure sensor 21, temperature sensor 22, and environmental pressure sensor 23, relayed through A/D converter 25 and stored in data logger 26 at this time is shown in FIGS. 3, 4 and 5. FIG. 3 shows water depth (converted from environmental pressure: m); FIG. 4 shows water temperature (° C.); and FIG. 5 shows primary pressure (kgf/cm$^2$) in the high pressure gas container. Time (min) is shown on the horizontal axis in each figure, with the measurements shown for an equivalent scale and elapsed time.

As clear from the graphs in FIGS. 3, 4 and 5, three dives indicated by the symbols (i)~(ii), (iii)~(iv), and (v)~(vi) in the figures were performed. The duration of the first dive was 8~10 minutes. As shown in FIG. 3, the water depth ranges from approximately 0~18m. The change in water temperature (° C.) during this time varied such as shown by the graph in FIG. 4, ranging above and below an average of 25° C. Variation in the primary pressure inside the high pressure gas container, which is the basis for calculating respiratory gas consumption during these dives, described a curve on the graph such as shown in FIG. 5. These graphic curves were clearly recorded and stored as data in the data logger.

Figure 6:
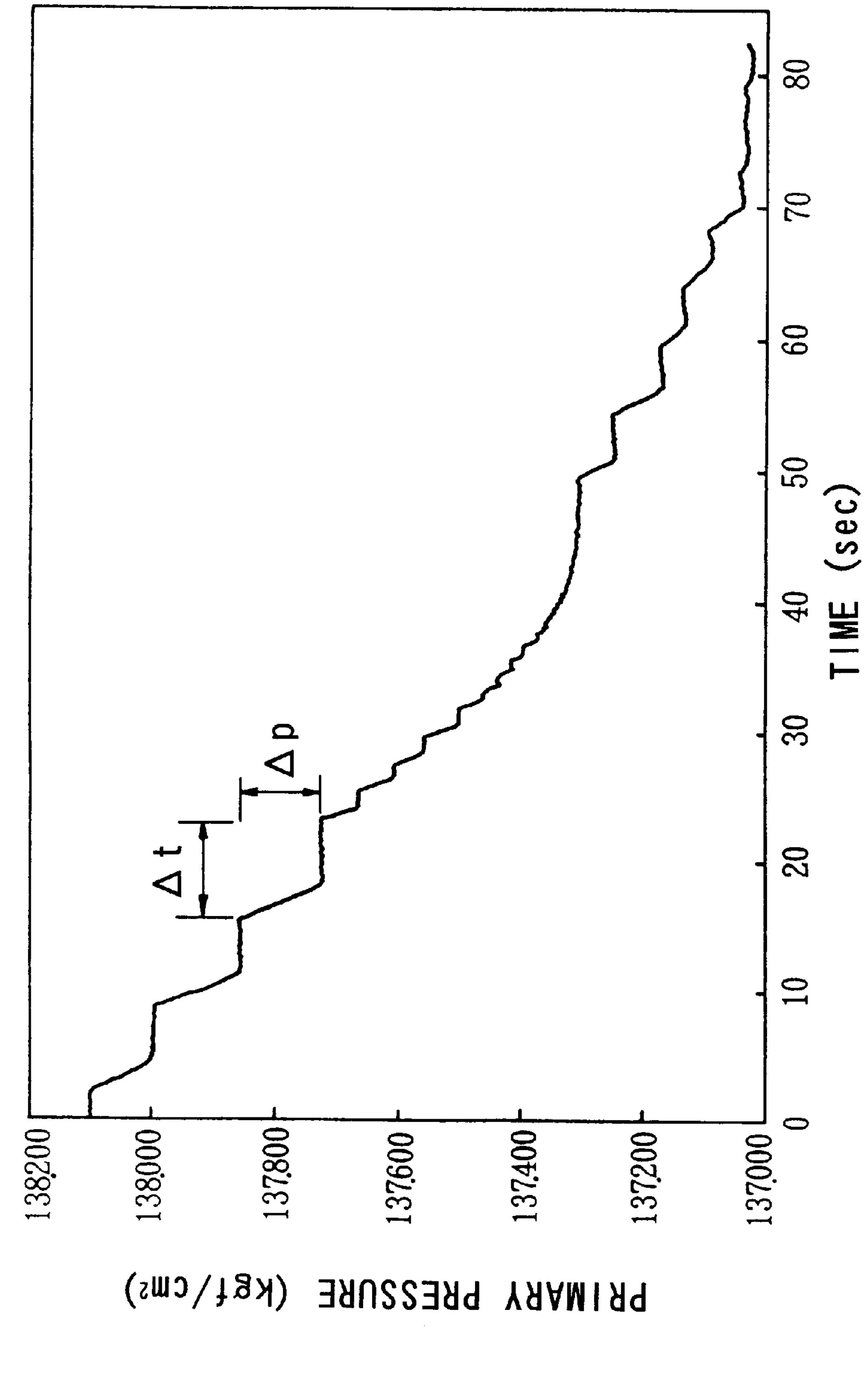
FIG. 6 is a graph of measurements of the primary pressure in a high pressure gas container at each breath when diving which were obtained in the examples employing the present invention's respiratory gas consumption monitoring device underwater.

FIG. 6 shows a graph in which the change in the primary pressure of the high pressure gas container each time the diver breaths during the dive is stored as data. The change in the primary pressure (kgf/cm$^2$) is shown on the vertical axis, while time (sec) is plotted on the horizontal axis. $\Delta P$ in the figure is the drop in pressure during one breath, while $\Delta t$ is the breathing duration (sec) of one breath. The progressive drop in the pressure of high pressure gas container, i.e., the primary pressure, with each breath can clearly be seen in FIG. 6.

A demand pressure regulator (corresponding to secondary pressure regulator 11 provided to the mask) used in scuba diving operates only during inhalation, allowing respiratory gas to flow in. The primary pressure regulator 4 attached to high pressure gas container 2 also operates at this time, with the pressure abruptly dropping. The demand pressure regulator does not operate from the end of inhalation through the duration of exhalation. Thus, there is no consumption of respiratory gas. For this reason, the primary pressure during this time maintains a constant value with respect to the elapsed time. Note that the gas expelled during exhalation is expelled to the outside via an expulsion valve on the demand pressure regulator. It was possible to clearly record and extract this type of variation in state, as shown in FIG. 6.

The interval of a single breath is the time duration until the next pressure drop begins. By analyzing the graph in FIG. 6 in detail, it is possible to discriminate between the time intervals for inhalation and exhalation. In addition, the diver's respiratory gas consumption with each breath can be calculated using $\Delta P$, and the values for the volume of the high pressure gas container, the environmental temperature (water temperature, for example), and environmental pressure (water depth for example). Moreover, the respiratory gas consumption is equivalent to the inhalation amount per breath. Thus, by employing this value in combination with the value of $\Delta t$, it may be used in the analysis and prediction of various breathing behaviors by the diver.

INDUSTRIAL APPLICABILITY

The present invention may be executed in the modes described above, and provides the effects as explained below.

It has been difficult to grasp the state of respiratory behavior for an active or working subject wearing one of the various breathing apparatuses described above using the conventional technology. The present invention was designed to enable the accurate collection and recording of data capable of rendering this possible. For example, in the field of diving there has not been an example of actual measurements made of skip breathing, or of the breathing which is deeper and slower than that performed on land which is carried out by a diver who is practicing buoyancy control (trimming) through respiration.

By measuring the variation in the primary pressure of the respiratory gas used to fill a high pressure gas container employed in a breathing apparatus that is carried by the user, the present invention makes it possible to accurately obtain the consumption of respiratory gas per breath taken by the user over time.

The measurement of the primary pressure of the respiratory gas is performed by disposing a primary pressure sensor to a high pressure opening at which the primary pressure gauge of a primary pressure adjusting device, for reducing the primary pressure of the gas used to fill the high pressure gas container, is connected, or by connecting a high pressure hose to this opening and then disposing a primary pressure sensor to this hose. Thus, the attachment and release of the sensor is convenient and easy, and a monitoring device can be provided which is lightweight and small in size, enabling portability. As a result, it is possible to measure the respiratory behavior of a user who is performing work or activities in the field, as well as to enable analysis and prediction of the respiratory behavior of such a user.

Moreover, monitoring of the measurement, analysis and prediction of the aforementioned respiratory behavior at a site removed from the location of activity by the user can be carried out with satisfactory accuracy by providing receiving and transmitting equipment. The present invention can also be effectively applied to the education and training of workers, as well as to safety management, technical evaluation of respiratory device functioning, etc., quality evaluation such as safety, etc., based on the measured data obtained using the present invention's monitoring method and monitoring device, and the analyzed and predictive data based thereon.

Moreover, the present invention's respiratory gas consumption monitoring device and monitoring method may be suitably employed for monitoring at any type of sites where a breathing apparatus is employed, such as, for example, during diving, in land disasters, in medical treatment (i.e., extraction of a life vitality signal using respiratory monitoring of a patient inhaling oxygen), in training to acclimate to low oxygen environments, or in monitoring in sports medicine.

In addition, by determining respiratory volume through the addition of this function to the dive computers which have spread in use in recent years, it is possible to more accurately manage decompression, so that the diver's safety is improved.

What is claimed is:

1. A respiratory gas consumption monitoring device (20) for a breathing apparatus (1) that reduces the pressure of a respiratory gas (G) supplied from a high pressure gas container (2) via the use of a pressure regulator (4), and supplies the gas to a breathing mask (10) worn by a user, comprising:

said respiratory gas consumption monitoring device (20) being connected by a hose (29) which is arranged before said pressure regulator (4) for introduction of the respiratory gas prior to the reduction in pressure from the high pressure gas container (2);

and said respiratory gas consumption monitoring device being integrally housed within a housing (28):

(a) a primary pressure sensor (21) for detecting the primary pressure in said high pressure gas container (2) before the pressure is reduced by said pressure regulator (4);

(b) an environmental pressure sensor (23) and a temperature sensor (22) for the purpose of correcting said primary pressure;

(c) an amplifier (24) for amplifying the signal detected by said primary pressure sensor (21);

(d) an A/D converter (25) for performing analog/digital conversion of said signal;

(e) a data logger (26) for storing said analog/digital converted signals; and (f) a display (27) for displaying the signals or data needed for monitoring the respiratory state of the user of the breathing apparatus.

2. A respiratory gas consumption monitoring device according to claim 1, characterized in that a computer (X), having at least one of the functions of calculating respiratory gas consumption, and analyzing and predicting respiratory behavior, may be provided connected to data logger (26), which stores the analog/digitally converted signals.

3. A respiratory gas consumption device according to claim 1, characterized in that a transmitting and receiving apparatus (Y) may be provided having a function for enabling transmission and reception of data at a site which is removed from the location of the user of the breathing apparatus.

4. A respiratory gas consumption monitoring device according to claim 1, characterized in that the signal and data displayed on display device (27) displays at least one signal and data for expressing the respiratory gas consumption state, respiratory behavior of the user of the breathing apparatus, or the environmental state at the location where the breathing apparatus is being used.

5. A respiratory gas consumption monitoring method for monitoring respiratory gas consumption in a breathing apparatus (1) in which the respiratory gas from a high pressure gas container (2) is communicated to a breathing mask (10) worn by the user after being reduced in pressure by a pressure regulator (4), characterized in that the respiratory gas consumption of the user wearing the breathing apparatus is measured by introducing the respiratory gas from said high pressure gas container (2) into respiratory gas consumption monitoring device (20) prior to reduction of the pressure by said pressure regulator (4), detecting changes in the primary pressure using a primary pressure sensor (21) integrally housed within a housing (28) of said monitoring device (20) and correcting the detected primary pressure based on the gas temperature detected by a temperature sensor (22) and the surrounding environmental pressure detected by a surrounding environmental pressure sensor (23) which are housed within the housing (28) of the monitoring device (20).

6. A respiratory gas consumption monitoring method characterized in that the pressure signal obtained when the primary pressure of said high pressure gas container (2) is detected prior to pressure reduction is amplified; said signal is analog/digitally converted at an A/D converter (25); and said analog/digitally converted signal, and the signals and data needed for monitoring the respiratory and physiological state of the user wearing the breathing apparatus, or for monitoring the respiratory state of the user under various environmental factors, are extracted.

7. A respiratory gas consumption monitoring method according to claim 6, characterized in that said analog/digitally converted signal, and data needed for monitoring, are extracted at a monitoring base which is at a site removed from the location of the user of the breathing apparatus.

* * * * *